US010569104B2

(12) United States Patent
El Fakhri et al.

(10) Patent No.: US 10,569,104 B2
(45) Date of Patent: Feb. 25, 2020

(54) SYSTEM AND METHOD FOR QUANTITATIVE MAPPING OF RADIOACTIVITY PRODUCTION RATE DURING PROTON THERAPY

(71) Applicant: The General Hospital Corporation, Boston, MA (US)

(72) Inventors: Georges El Fakhri, Brookline, MA (US); Nathaniel Alpert, Plymouth, MA (US); Xuping Zhu, Malden, MA (US); Kira Grogg, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 570 days.

(21) Appl. No.: 15/095,827

(22) Filed: Apr. 11, 2016

(65) Prior Publication Data

US 2016/0296766 A1 Oct. 13, 2016

Related U.S. Application Data

(60) Provisional application No. 62/145,037, filed on Apr. 9, 2015.

(51) Int. Cl.
*A61N 5/10* (2006.01)

(52) U.S. Cl.
CPC .... *A61N 5/1071* (2013.01); *A61N 2005/1052* (2013.01); *A61N 2005/1087* (2013.01)

(58) Field of Classification Search
CPC .......... A61N 5/1071; A61N 2005/1052; A61N 2005/1087
See application file for complete search history.

(56) References Cited

U.S. PATENT DOCUMENTS

2015/0231411 A1\* 8/2015 O'Neal, III ............ H05H 13/04
600/1
2018/0021005 A1\* 1/2018 Conner ................... A61B 6/00
600/431

OTHER PUBLICATIONS

Sportelli et al. "First full-beam PET acquisitions in proton therapy with a modular dual-head dedicated system", Phys. Med. Biol. 59 (2014) pp. 43-60.\*
Huesman et al. "Kinetic parameter estimation from SPECDT cone-beam projection measurements", Phys. Med. Biol. 43 (1998) pp. 973-982.\*

(Continued)

*Primary Examiner* — Kaylee R Wilson
(74) *Attorney, Agent, or Firm* — Quarles & Brady LLP

(57) ABSTRACT

The present disclosure provides a system and method for method for quantifying radioactivity production during a proton treatment of a patient. In some aspects, a method includes administering, using a proton delivery system, a proton treatment using at least one therapeutic proton beam generating positron emitting radionuclides within a region of interest (ROI) of a patient, and acquiring, using an emission tomography system, emission tomography data indicative of an activity of the positron emitting radionuclides in the ROI. The method also includes quantifying, based on a kinetic model, a radioactivity production rate of at least one positron emitting radionuclide using the emission tomography data. The method further includes generating at least one map indicative of the radioactivity production rate of the at least one positron emitting radionuclide.

38 Claims, 11 Drawing Sheets

(56) References Cited

OTHER PUBLICATIONS

Zhu et al. "Verification of proton therapy with PET: A kinetic modeling approach", J Nucl Med; vol. 53, No. supplement 1, p. 264. (Year: 2012).*

Zhu et al. "Proton Therapy Verification with PET Imaging", Theranostics, 3(10):731-740 (Year: 2013).*

Attanasi, F. et al. "Extension and validation of an analytical model for in vivo PET verification of proton therapy—a phantom and clinical study" Phys. Med. Biol. 2011;56:5079-5098.

España, S. et al. "Reliability of proton-nuclear interaction cross section data to predict proton-induced PET images in proton therapy" Phys. Med. Biol. 2011;56:2687-2698.

Fiedler, F. et al. "On the effectiveness of ion range determination from in-beam PET data" Phys. Med. Biol. 2010;55:1989-98.

Fischman, A. J. et al. "Regional measurement of canine skeletal muscle blood flow by positron emission tomography with H2 15O" J. Appl. Physiol. 2002;92:1709-16.

Min, C. H. et al. "Clinical Application of in-room PET for in vivo Treatment Monitoring in Proton Radiotherapy" Int. J. Rad. Oncol. Biol. Phys. 2013;86:183-189.

Paganetti, H. "Range uncertainties in proton therapy and the role of Monte Carlo simulations" Phys. Med. Biol. 2012;57:R99-R117.

Parodi, K. et al. "Patient study of in vivo verification of beam delivery and range, using positron emission tomography and computed tomography imaging after proton therapy" Int. J. Rad. Oneal. Biol. Phys. 2007;68:920-934.

Parodi,K. et al. "PET/CT imaging for treatment verification after proton therapy: a study with plastic phantoms and metallic implants" Med. Phys. 2007;34:419-435.

Perl, J. et al.TOPAS: An innovative proton Monte Carlo platform for research and clinical applications 2012;39:6818-6837.

Schneider, W. et al. "Correlation between CT numbers and tissue parameters needed for Monte Carlo simulations of clinical dose distributions" Phys. Med. Biol. 2000;45:459-478.

Enghardt, W. et al. "Dose quantification from in-beam positron emission tomography" Radiother. Oncol. 2004;73:S96-98.

España, S. et al. "The impact of uncertainties in the CT conversion algorithm when predicting proton beam ranges in patients from dose and PET-activity distributions" Phys. Med. Biol. 2010;55:7557-71.

Hsi, W. et al. "In vivo verification of proton beam path by using post-treatment PET/CT imaging" Med. Phys. 2009;36:4136-4146.

Iseki, Y. et al. "Positron camera for range verification of heavy-ion radiotherapy" Nucl. Instruments Methods Phys. Res. Sect. A Accel. Spectrometers, Detect. Assoc. Equip. 2003;515:840-849.

Knopf, A. et al. "Systematic analysis of biological and physical limitations of proton beam range verification with offline PET/CT scans" Phys. Med. Biol. 2009;54:4477-4495.

Miyatake, A. et al. "Measurement and verification of positron emitter nuclei generated at each treatment site by target nuclear fragment reactions in proton therapy" Med. Phys. 2010;37:4445-4455.

Mizuno, H. et al. "Washout measurement of radioisotope implanted by radioactive beams in the rabbit" Phys. Med. Biol. 2003;48:2269-2281.

Nishio, T. et al. "Dose-volume delivery guided proton therapy using beam on-line PET system" Med. Phys. 2006;33:4190.

Parodi, K. et al. "Comparison Between In-Beam and Offline Positron Emission Tomography Imaging of Proton and Carbon Ion Therapeutic Irradiation at Synchrotron- and Cyclotron-Based Facilities" Int. J. Rad. Oneal. Biol. Phys. 2008;71:945-956.

Parodi, K. et al. "Potential application of PET in quality assurance of proton therapy" Phys. Med. Biol. 2000;45:N151-6.

Senda, M. et al. "Regional perfusion, oxygen metabolism, blood volume and immunoglobulin G accumulation at focal sites of infection in rabbits" Eur. J. Nucl. Med. 1992;19:166-72.

* cited by examiner

SYSTEM AND METHOD FOR QUANTITATIVE MAPPING OF RADIOACTIVITY PRODUCTION RATE DURING PROTON THERAPY

CROSS-REFERENCE TO RELATED APPLICATIONS

This application claims the benefit of, and incorporates herein in its entirety, U.S. Provisional Patent Application Ser. No. 62/145,037 filed on Apr. 9, 2015 and entitled "QUANTITATIVE MAPPING OF RADIOACTIVITY PRODUTION RATE DURING PROTON THERAPY."

STATEMENT REGARDING FEDERALLY SPONSORED RESEARCH

This invention was made with government support under grant numbers EB012823 and EB019959 awarded by the National Institutes of Health. The government has certain rights in the invention.

BACKGROUND OF THE INVENTION

The field of the invention relates to systems and methods for ionizing radiation treatment. More particularly, the invention relates to systems and methods for improved proton therapy.

Proton therapy systems takes advantage of the energy deposition profile of high energy protons in tissue to provide highly conformal exposure of tumors while sparing critical structures. Specifically, protons have a finite penetration depth in dependence of their energy, as shown in FIG. 1A. In contrast to a photon beam 100 in conventional radiotherapy, the radiation dose delivered by a mono-energetic proton beam 102 is maximal within a short distance of a proton's end range in tissue, known as the Bragg peak 104. Superficial tissues receives less radiation dose compared to those at the Bragg peak. In addition, the dose profile drops dramatically beyond the Bragg peak, with tissues receiving practically no radiation dose thereafter. Such dose deposition characteristics allows high doses to be delivered to deep-seated tumors while reducing normal tissue doses and toxicities.

To provide volume coverage to a target 106, often a combination 108 of multiple proton beams with different energies are utilized, resulting in a spread-out Bragg peak 110. However, this comes at the cost of increased superficial tissue doses, as appreciated form FIG. 1A. Regardless of whether single or multi-energy beams are used, due to the steep dose drop-off near the Bragg peak, proton range errors are often of concern. This is especially important when critical structures are located just beyond the target 106. As such, range inaccuracy could result increased toxicities due to critical structures receiving close to a full dose, or tumors receiving suboptimal coverage.

During proton therapy, positron emitting radionuclides, such as 15-O, 13-N and 11-C, are produced through nuclear fragmentation reactions. Therefore, positron emission tomography (PET) imaging of the activity distribution of these proton induced positron emitters has emerged as a possible approach for in vivo proton therapy verification. Specifically, the spatial distribution of the produced positron emitters is related to proton fluence, nuclear reaction cross-sections and target nuclide concentration distributions. As such, local intensities of PET images obtained after treatment can identify the extent of the irradiated tissue and some kind of distal activity threshold can help define proton beam range errors.

However, as shown in FIG. 1B, PET activity as a function of depth differs from the dose distribution, since these are produced through very different physical processes. Therefore, any verification of a proton treatment plan and beam delivery must be carried out indirectly. To do this, current approaches generate production maps of different radionuclide species by performing Monte Carlo (MC) simulations based on treatment planning information and tissue composition maps obtained from CT images. However, in addition to radioactive decay, biological processes complicate the prediction of deposited dose, beam range, and radioactivity because simple analysis of PET image intensities do not distinguish between biological washout and an absence of dose deposition. In particular, it is known that biological washout can dramatically change the original proton induced activity distribution, particularly in soft tissues. Therefore, production maps are often corrected for radioactive decay and biological washout to generate a predicted PET activity distribution.

In one previous approach, correction of the production maps utilizes a model that includes nominal values for biological clearance applied retrospectively to the MC data. Specifically, thresholds on the treatment-CT image numbers are set to identify fat, soft tissue, bone, cortical bone, muscle and brain tissues. The washout in each tissue type is then decomposed into three components, namely fast, medium and slow. Fractions and biological half-lives are assigned to each component in each tissue type, based on animal study results with stable and radioactive carbon ion beams. After applying radioactive decay corrections and predefined nominal biological washout corrections, distributions from different radionuclides are then summed to form predicted PET activity distributions, which are then compared with static PET images.

This approach has several limitations that prevents accurate verification of proton therapy. First, model parameters adopted above are from carbon-beam studies, making their applicability to proton beam therapy questionable. This is because projectile fragmentation is more important in carbon ion therapy, while only target fragmentation is possible in proton therapy. That is, in carbon beam therapy, 11-C obtained from projectile fragmentation is the dominant radionuclide, while in proton therapy, 15-O obtained from target fragmentations reactions has the highest yield. Second, the approach above does not account for varied washout rates of radionuclides incorporated as different molecular species. In fact, the CT number is insufficient to fully characterize the tissue environment, since the chemical form of a product determines its biological fate. Third, biological clearance is greatly affected by the prevailing biological environment, such as local vascular development, tissue heterogeneity and perfusion rate, not to mention prior chemotherapy or radiation treatment. As such, clinical studies have shown that biological washout was one of the major reasons for the discrepancies between the measured and simulated ranges when the proton beam stops in soft tissue.

Hence, there is a need for systems and methods for use in identifying and mitigating errors in order to deliver precise and predictable proton therapy with the highest clinical benefit.

SUMMARY OF THE INVENTION

The present disclosure overcomes the aforementioned drawbacks by providing a system and method directed to improving proton treatment. In particular, a novel approach is provided whereby radioactivity production and clearance generated during the course of proton treatment can be mapped directly from dynamic emission tomography measurements, such as positron emission tomography (PET) measurements.

In one aspect of the present disclosure, a method for quantifying radioactivity production during a proton treatment of a patient. In some aspects, a method includes administering, using a proton delivery system, a proton treatment using at least one therapeutic proton beam generating positron emitting radionuclides within a region of interest (ROI) of a patient, and acquiring, using an emission tomography system, emission tomography data indicative of an activity of the positron emitting radionuclides in the ROI. The method also includes quantifying, based on a kinetic model, a radioactivity production rate of at least one positron emitting radionuclide using the emission tomography data. The method further includes generating at least one map indicative of the radioactivity production rate of the at least one positron emitting radionuclide.

In another aspect of the present disclosure, a system for quantifying radioactivity production during a proton treatment of a patient. The system includes a proton delivery system configured to deliver a proton treatment using at least one therapeutic proton beam generating positron emitting radionuclides within a region of interest (ROI) of a patient, and an emission tomography system configured to acquire emission tomography data indicative of an activity of the positron emitting radionuclides. The system also includes a computer configured to receive the emission tomography data, and quantify, based on a kinetic model, a radioactivity production rate of at least one positron emitting radionuclide using the emission tomography data. The computer is also configured to generate at least one map indicative of the radioactivity production rate of the at least one positron emitting radionuclide.

In yet another aspect of the present disclosure, a non-transitory, computer-readable storage medium is provided. The computer-readable storage medium includes therein instructions that, when executed by a computer processor, cause the computer processor to generate a report indicative of radioactivity production during a proton treatment of a patient. The instructions include accessing emission tomography data indicative of an activity of the positron emitting radionuclides generated in a region of interest (ROI) of a patient using at least one therapeutic proton beam. The instructions also quantifying, based on a kinetic model, a radioactivity production rate of at least one positron emitting radionuclide using the emission tomography data. The instructions further include generating a report indicative of the radioactivity production rate of the at least one positron emitting radionuclide.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Although protons can potentially deliver much higher doses to tumors, as compared with photon-based treatments, while keeping dose to normal tissues low, it is more sensitive to uncertainties. This could lead to local treatment failure and normal tissue over-dose. For example, many lung cancer patients succumb to the disease after radiation therapy due to local disease recurrence. Over-irradiating critical normal tissues can increase the risk of severe adverse effects, such as esophagitis, myelitis, brachial plexopathy, pneumonitis, pulmonary fibrosis, cardiac toxicity, and secondary cancers. Better preservation of critical normal tissues would decrease morbidity and result in better quality of life for patients. In addition, possible severe toxic effects compromise the delivery of cancer radiotherapy, because dose reductions necessary to allow for the resolution of side effects reduce the effectiveness of the therapy.

This present disclosure introduces a novel and innovative approach designed to overcome the limitations of previous technologies associated proton therapy. In particular, a system and method are described quantifying radioactivity production and clearance rates of positron emitting radionuclides, such as 15-O, generated during proton treatment. Using a kinetic model, radioactivity production rate maps, or distribution of total activity produced during irradiation, can be directly estimated on a voxel-by-voxel basis from dynamic PET reconstructions. By contrast, previous approaches focused solely on the clearance of radionuclides, while disregarding the input rate of energy to irradiated tissue. However, the present disclosure recognizes that measured radionuclide concentrations represent a balance between build-up due to irradiation, and clearance due to both radioactive decay and biological elimination.

As appreciated from descriptions below, the provided system and method may utilize information obtained from mapped radioactivity production and clearance to assess the delivered treatment. For example, proton range of delivered beams may be determined, in order to potentially adapt a treatment plan in subsequent fractions. In addition, such information may also be used to determine a response of the patient to the proton treatment.

Figure 1A:
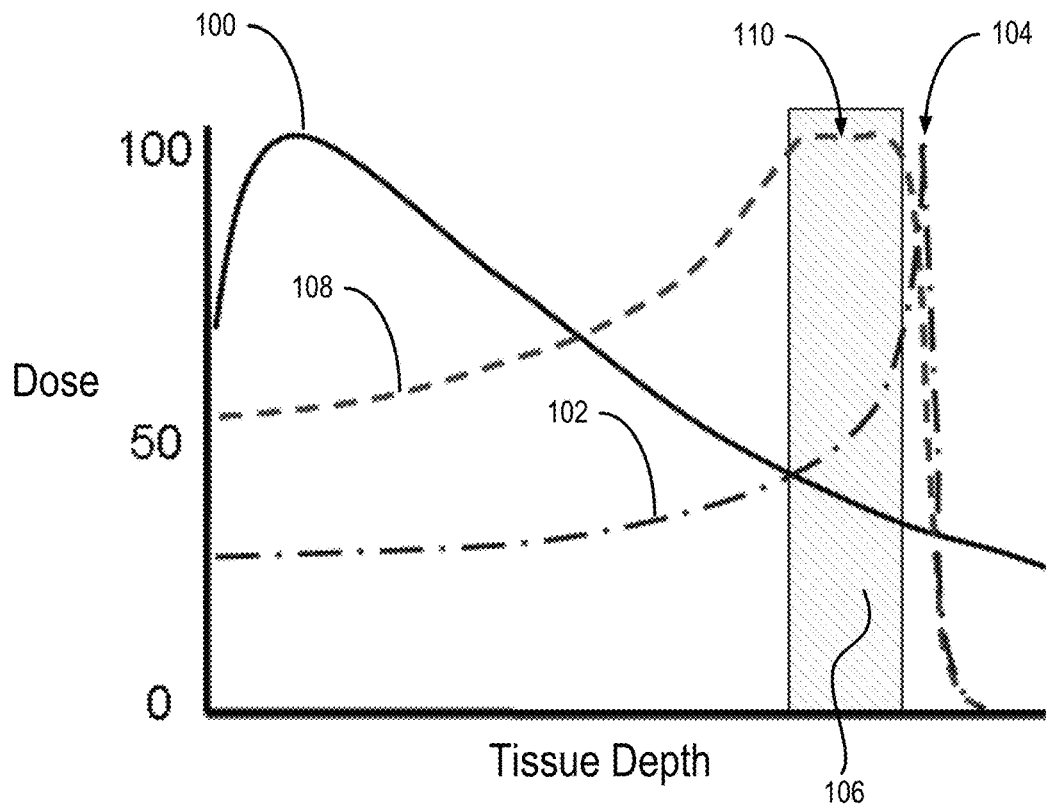
FIG. 1A is a graph comparing depth-dose profiles for photon and proton therapies.
Figure 1B:
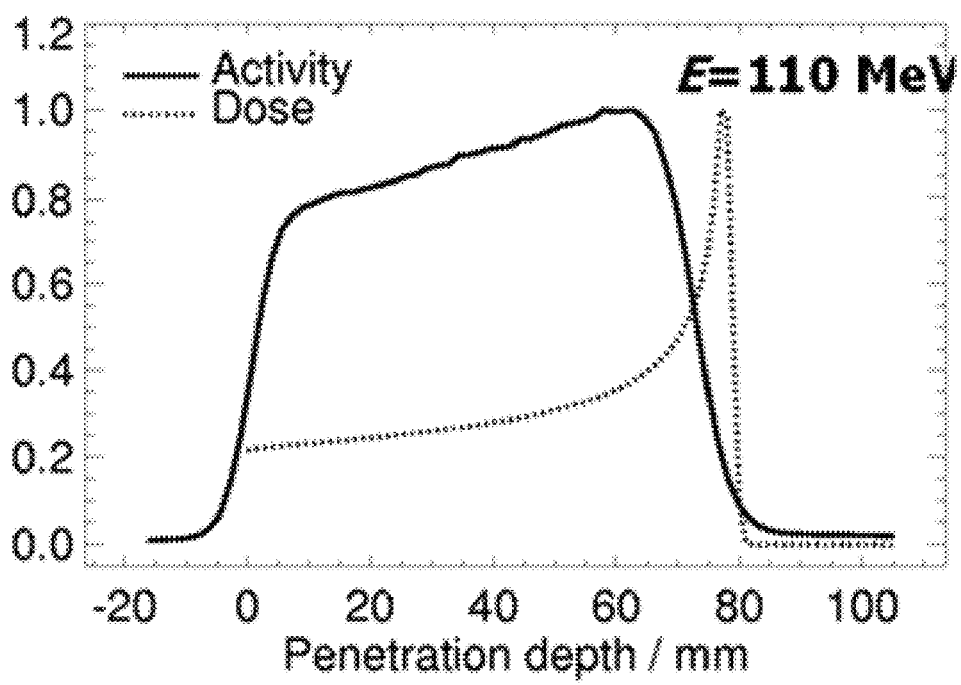
FIG. 1B is a graph comparing induced radioactivity and dose deposition with tissue depth.
Figure 2:
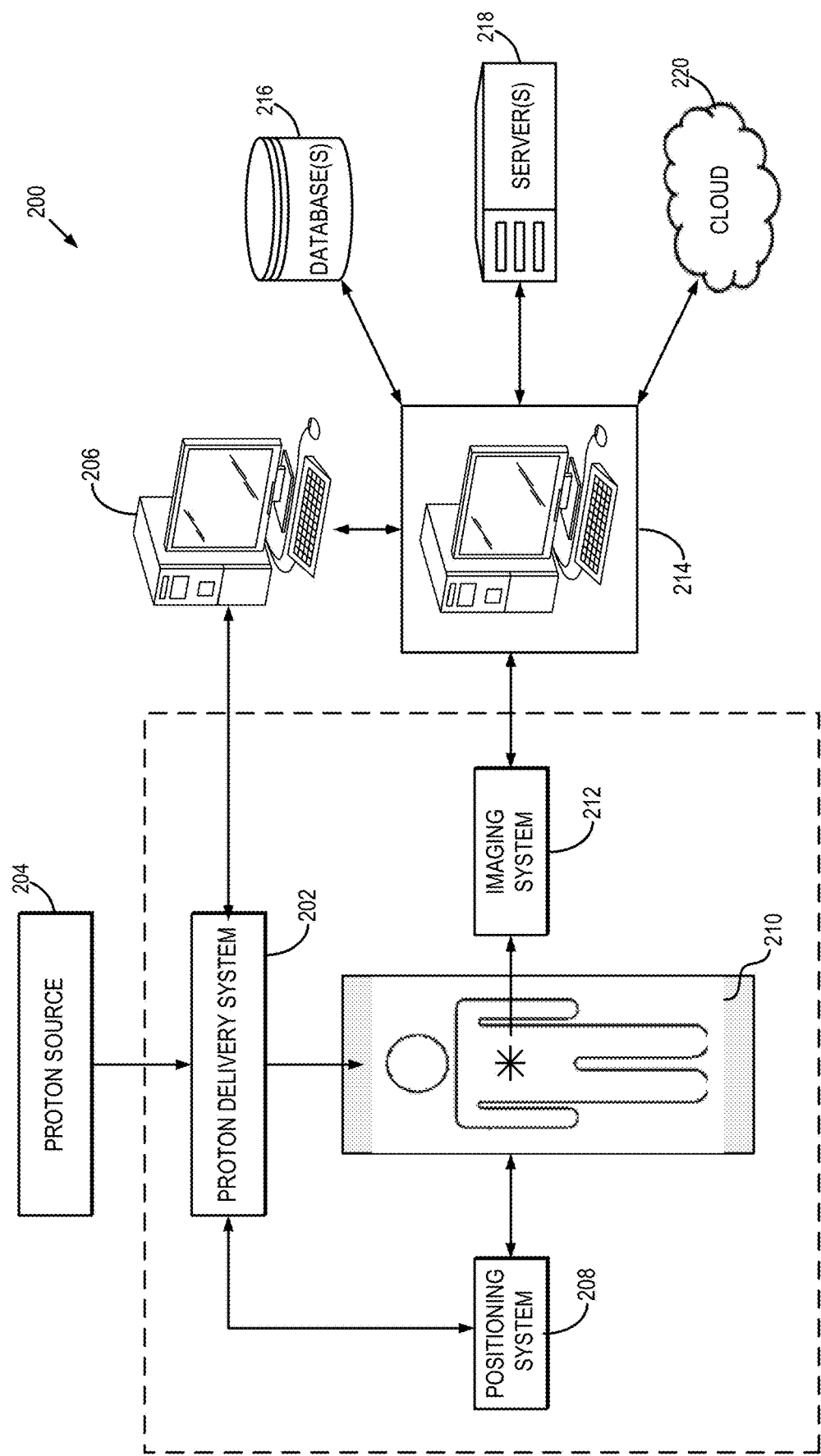
FIG. 2 is a schematic illustration of an example proton treatment system, in accordance with aspects of the present disclosure.

Referring particularly to FIG. 2, a proton treatment system 200, in accordance with aspects of the present disclosure, is shown. In general, the proton treatment system 200 includes a proton delivery system 202 that is configured to deliver high energy protons obtained from a proton source 204, such as a cyclotron or synchrotron. Proton treatment generally involves executing a proton treatment plan, provided via a treatment console 206, that is optimized to provide a conformal radiation dose to target tissues while avoiding critical structures. Typically, the treatment console 206 receives the treatment plan from a planning workstation (not shown in FIG. 2), that need not be at the same location.

During a treatment session, the proton delivery system 202 can build a radiation dose distribution inside a patient using various treatment fields aimed from different directions. The durations, shapes, and energies of the proton beams would then determine the dose extent and dose profiles in the patient. In cooperation with a positioning system 208, which controls the position and orientation of a treatment table on which a patient rests, conformal radiation dose can be delivered from multiple directions about the patient. In some aspects, the positioning system 208 may be configured to move the patient to the imaging system 212.

As shown in FIG. 2, the proton treatment system 200 also includes an imaging system 212. In accordance with aspects of the present disclosure, the imaging system 212 can be an emission tomography system configured to acquire emission tomography data indicative of an activity of positron emitting radionuclides generated during treatment. By way of example, the emission tomography system can be a positron emission tomography (PET) system, a single photon emission computed tomography (SPECT) system, a hybrid computed tomography (CT)/PET system, or a hybrid magnetic resonance (MR)/PET system, and others.

Although in FIG. 2, the proton delivery system 202 and imaging system 212 are shown as different systems, it is readily apparent that these could be integrated into one hybrid system. In this manner, these systems would share the same coordinate system, allowing emission tomography data to be acquired during the proton treatment, without need for moving the patient. For example, emission tomography data may be acquired between treatment fields. Also, such integrated system would be advantageous in minimizing the time interval between treatment and imaging.

In some implementations, the imaging system 212 is connected to a processor 214, which as shown in FIG. 2, can be a computer or workstation, as well as a network server, a mainframe or any other general-purpose or application-specific computing device. The processor 214 may also be part of or include a portable device, such as a mobile phone, laptop, tablet, personal digital assistant ("PDA"), multimedia device, or any other portable device. As such, the processor 214 may also operate as part of, or in collaboration with one or more computers, systems, devices, machines, mainframes, servers and the like. The processor 214 may operate autonomously or semi-autonomously, receiving instructions from a memory, a user, as well as any other source logically connected thereto, such as another networked computer, device or server. In this regard, the processor 214 may be any computing device, apparatus or system having one or more processing units, and designed to integrate a variety of software and hardware capabilities and functionalities, as well as configured for carrying out steps in accordance with aspects of the disclosure. Example processing units may include CPUs, GPUs and the like.

The processor 214 may also be in communication with various other external computers, systems and devices including one or more databases 216, servers 218 and cloud 220, as well as the treatment console 206 or a treatment planning station. As such, processor 214 may be configured to exchange a wide variety of information and data. For example, the processor 214 may be configured to access patient data, including various representations, or images obtained from patient, such as CT, MR, or PET images, as well as information related to target structures, critical structures, treatment plans, and on. In some aspects, the processor 214 may be configured to access emission tomography data acquired during or following a proton treatment from the imaging system 212, as well as database 216 or data storage server.

The processor 214 may include various input elements for receiving emission tomography data, and other data. Input elements may also be configured to receive information or data directly from the imaging system 212 or another imaging system, as well as from one or more data servers, databases, cloud, internet and so forth, as indicated in FIG. 2. Example input elements may include flash-drives, CD or DVD drives, USB or micro-USB inputs, HDMI inputs, an Ethernet or WIFI connection, and other inputs for receiving computer-readable media, data or signals. The processor 214 may also include input elements configured to receive a variety of information, data or selections from a user. Example input elements may include a mouse, keyboard, touchpad, touch screen, buttons, and the like.

In addition to other processing tasks, the processor 214 is configured to receive the emission tomography data and quantify, based on a kinetic model, a radioactivity production rate of at least one positron emitting radionuclide using the data. The processor 214 is further configured to generate at least one map indicative of the radioactivity production rate and clearance rate of the at least one positron emitting radionuclide within a region of interest (ROI) of a patient, generated using at least one therapeutic proton beam. Example positron emitting radionuclides include 15-O, 13-N, and 11-C. The generated maps may be one-dimensional (1D), two-dimensional (2D) or three-dimensional (3D). In some aspects, the processor 214 may also be configured to utilize acquired or accessed emission tomography data, to generate a time series of emission tomography images. In addition, the processor 214 may also be configured perform an image registration between various generated maps and images, including CT, MR, and PET images.

In some aspects, the processor 214 may be configured to analyze the maps generated in order to determine information associated with a proton treatment. For example, such information may include a penetration depth, or spread, of one or more therapeutic proton beams in a region or volume of interest. Other information may include a water clearance rate. Such information may be utilized to assess a proton treatment, or treatment fraction, and potentially adapt the treatment plan or delivery method. Such information may also be used to determine a risk for complications or toxicity to critical structures. In addition, information determined from the analysis may be used to determine a response of the patient to the proton treatment.

The processor 214 may also include one or more memory elements. Such memory elements may be in the form of transitory and non-transitory, computer-readable storage media having instructions therein for processing various data and information. In some aspects, non-transitory, computer-readable storage media include instructions that, when executed by one or more processing units of the processor 214, quantify, based on a kinetic model, a radioactivity production rate and clearance of at least one positron emitting radionuclide using the emission tomography data, and generate a report, based on the quantification, providing a wide variety of information, as described. In some aspects, the report may be in the form of an audio or visual alarm indicating, for example, an unsafe treatment, or a proton beam range exceeding a threshold value.

The processor 214 may also include various output elements for providing a report to a user or other system or device As such, the processor 214 may also be configured to send a wide variety of information and data to external systems, computers and devices. For example, the processor 214 may provide a report that includes information generated based on an analysis of emission tomography data acquired during or following a proton treatment.

Figure 3:
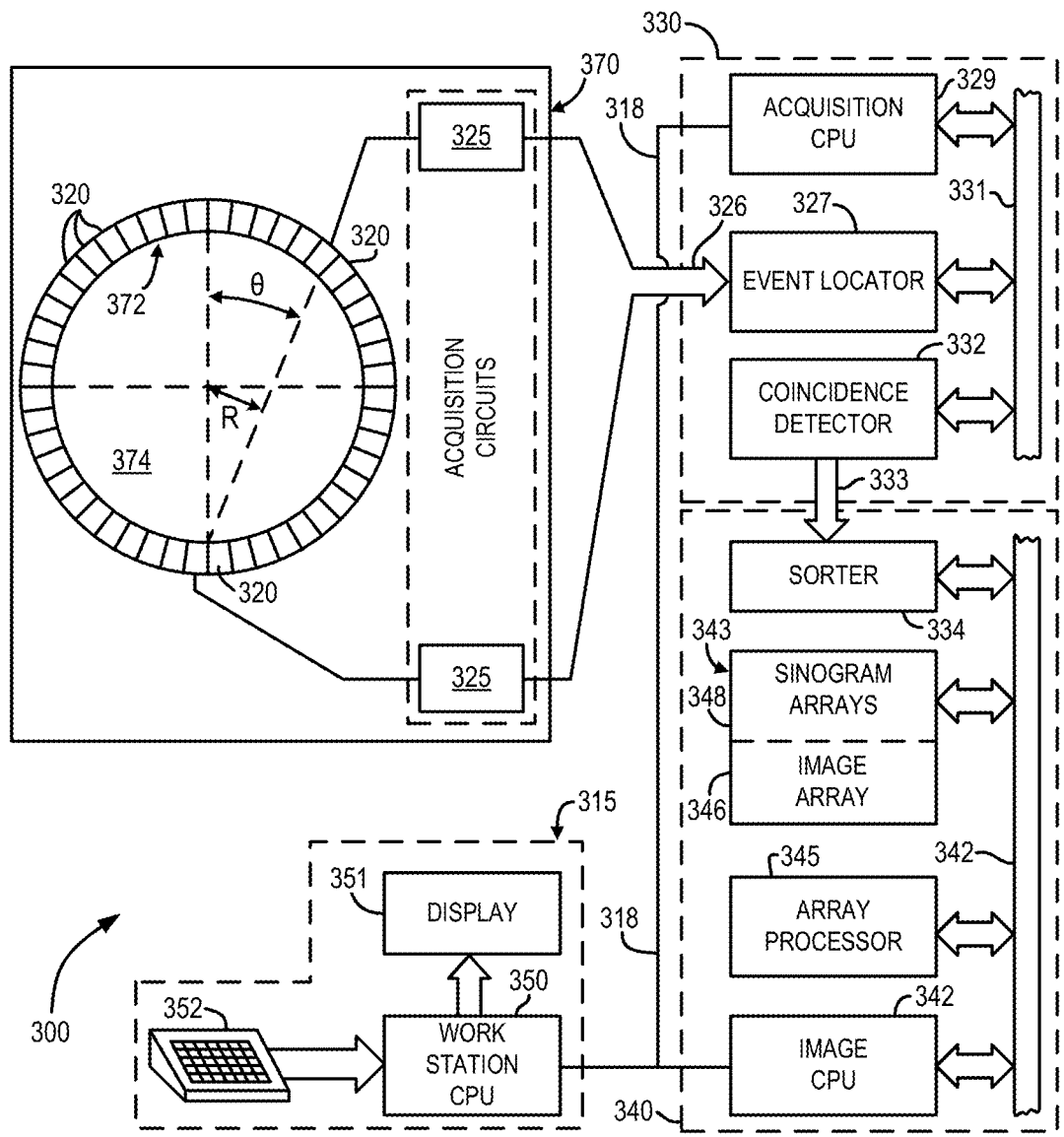
FIG. 3 is a schematic illustration of a positron emission tomography (PET) system, in accordance with the present disclosure.

Referring particularly to FIG. 3, a schematic diagram of a PET system 300 is shown. Although PET system 300, as represented in the example of FIG. 3, can be implemented as a stand-alone imaging system, in accordance with some aspects of the present disclosure, it may be appreciated that PET system 300 may also utilized in combination with other imaging systems. For example, PET system 300 may be integrated into a multi-modality, or hybrid, imaging system, such as a CT/PET system, or a MR/PET system. In some aspects, raw or processed PET data, or images, generated using PET system 300 may be directly used to generate photon attenuation maps, and/or attenuation-corrected images. In other aspects, raw or processed PET data, or images, may be combined with information from other raw or processed data or images, such as CT or MR data or images, to generate photon attenuation maps, and/or attenuation-corrected images.

As illustrated in FIG. 3, PET system 300 includes a gantry 370, which supports a detector ring assembly 372. The detector ring 372 includes detector units 320. The signals produced by the detector units 320 are then received by a set of acquisition circuits 325, which produce digital signals indicating the line of response and the total energy. These signals are sent through a communications link 326 to an event locator circuit 327. Each acquisition circuit 325 also produces an event detection pulse ("EDP") which indicates the exact moment the scintillation event took place.

The event locator circuits 327 form part of a data acquisition processor 330, which periodically samples the signals produced by the acquisition circuits 325. The processor 330 has an acquisition CPU 329 which controls communications on local area network 318 and a backplane bus 331. The event locator circuits 327 assemble the information regarding each valid event into a set of digital numbers that indicate precisely when the event took place and the position of the scintillator crystal which detected the event. This event data packet is conveyed to a coincidence detector 332 which is also part of the data acquisition processor 330.

The coincidence detector 332 accepts the event data packets from the event locators 327 and determines if any two of them are in coincidence. Coincidence is determined by a number of factors. First, the time markers in each event data packet must be within a preset time of each other, and second, the locations indicated by the two event data packets must lie on a straight line. Events that cannot be paired are discarded, but coincident event pairs are located and recorded as a coincidence data packet.

The coincidence data packets are conveyed through a link 333 to a sorter 334 where they are used to form a sinogram. The sorter 334 forms part of an image reconstruction processor 340. The sorter 334 counts all events occurring along each projection ray (R, θ) and organizes them into a two dimensional sinogram array 348 which is stored in a memory module 343. In other words, a count at sinogram location (R, θ) is increased each time a coincidence data packet at that projection ray is received.

The image reconstruction processor 340 also includes an image CPU 342 that controls a backplane bus 341 and links it to the local area network 318. An array processor 345 also connects to the backplane 341 and it reconstructs an image from the sinogram array 348. The resulting image array 346 is stored in memory module 343 and is output by the image CPU 342 to the operator work station 315.

The image reconstruction processor 340 may be configured to process acquired TOF-PET data by estimating from the TOF-PET data, in accordance with aspects of the present disclosure, a posterior probability distribution of attenuation-corrected TOF-PET data. For example, the image reconstruction processor 340 may obtain sample values of the posterior probability distribution by applying a Markov Chain Monte Carlo technique.

In some aspects, the image reconstruction processor 340 may be configured to produce one or more attenuation maps by computing one of a mean of the posterior probability distribution, or a marginalized median of the posterior probability distribution, or a marginalized maximum of the posterior probability distribution. In other aspects, the image reconstruction processor 340 may be configured to reconstruct attenuation-corrected images from the posterior probability distribution of attenuation-corrected TOF-PET data. Specifically, the image reconstruction processor 340 is configured to reconstruct images having voxels that contain attenuation-corrected estimates of a number of emissions per voxel, and produce from these images, images having voxels that contain attenuation-corrected estimates of activity.

The operator work station 315 includes a CPU 350, a display 351 and a keyboard 352. The CPU 350 connects to the network 218 and it scans the keyboard 252 for input information. Through the keyboard 352 and associated control panel switches, the operator can control the calibration of the PET scanner and its configuration. Similarly, the operator can control the display of the resulting image on the display 351 and perform image enhancement functions using programs executed by the work station CPU 350.

Figure 4:
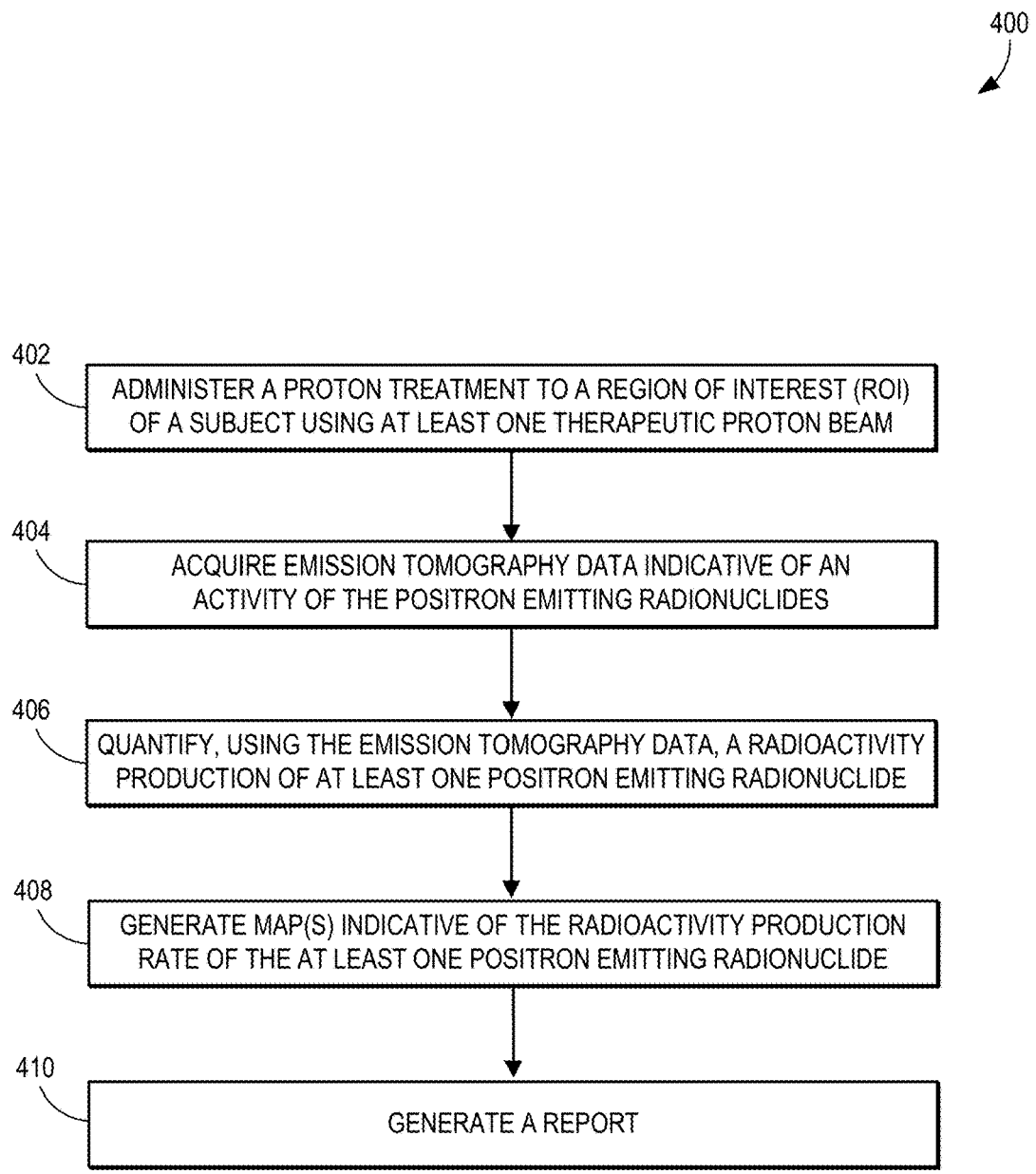
FIG. 4 is a flowchart setting forth steps of a process, in accordance with aspects of the present disclosure.

Referring now to FIG. 4, steps of a process 400 in accordance with aspects of the present disclosure are described. The process 400 may be carried out using a proton treatment system 200, as described with reference to FIG. 2, or any other suitable system.

The process 400 may begin at process block 402 with administering a proton treatment including one or more therapeutic proton beams or treatment fields to a region of interest (ROI) of a patient. One of ordinary skill in the art would recognize that administering such proton treatment includes generating one or more sets of planning images, including CT images, and creating a treatment plan.

As described, during proton therapy, positron emitting radionuclides, such as 15-O, 13-N and 11-C, are produced through nuclear fragmentation reactions. As such, emission tomography data indicative of the activity of the generated positron emitting radionuclides in the ROI are acquired at process block 404 for a period of time, using an emission tomography system, such as a PET system, SPECT system, hybrid CT/PET system, or a hybrid MR/PET system.

In some aspects, the emission tomography data acquired at process block 404 may be obtained during the proton treatment. For instance, emission tomography data may be acquired between different fields. Alternatively, the emission tomography data may be acquired after a preselected time interval following the proton treatment. For example, the preselected time interval may be up to 20 minutes, although other time intervals may be possible. In some aspects, the preselected time interval may be selected to maximize emission tomography signals from 15-O, or other positron emitting nuclides.

Then, at process block 208, based on a kinetic model, a radioactivity production rate of at least one positron emitting radionuclide may be quantified using the acquired emission tomography data, as will be described. In some aspects, a radioactivity clearance rate may also be quantified at process block 406. In some aspects, a time series of emission tomography images, including PET images, may be generated at process block 406 using the emission tomography data.

One or more maps indicative of the radioactivity production rate, as well as the radioactivity clearance rate, for one or more positron emitting radionuclides may then be generated, as indicated by process block 408. The generated maps may be one-dimensional (1D), two-dimensional (2D) or three-dimensional (3D). In some aspects, a comparison of maps generated according to process blocks 402 through 408 may be made using maps produced from a Monte Carlo approach. The comparison may also be made using information from another reference, or baseline measurements. Generated maps may be analyzed to produce various information associated with the administered proton therapy. For instance, penetration depth, dose spread, dose profile, and so forth, associated with one or more therapeutic proton beams in a region or volume of interest may be determined. Such information may be utilized to assess a proton treatment, or treatment fraction, as well as potentially adapt the treatment plan or delivery method. Also, generated information may be used to determine a risk for complications or toxicity to critical structures. In some aspects, generated information may be used to determine a response of the patient to treatment. As such, a water clearance rate may be determined.

Then a report may be generated at process block 410. The report may be in any form, and include various maps, images, and various information. As described, such information may include a penetration depth, dose spread, dose profile associated with one or more therapeutic proton beams in tissue, radioactivity production rates and clearance rates for one or more positron emitting radionuclides, a water clearance rate, a risk for complication or toxicity, a treatment response, and so forth. The report may be provided to a user, clinician, or relayed to a treatment planning system or workstation.

A kinetic model for the production and clearance of radioactivity, in accordance with aspects of the present disclosure, is now described. Specifically, the radionuclides produced from the nuclear fragmentation reactions, such as 15-O, 13-N and 11-C, and so forth, are initially in the free ion form but soon, typically within milliseconds, combine with a nearby ion/molecule to form a new molecule. The labeled molecule will be eliminated from the reaction volume by two mechanisms, radioactive decay and biological washout. The concentration of the $i^{th}$ labeled molecule, $C_i$ can be described with the following equation:

$$\frac{dC_i}{dt} = R_0(t) - k_i C_i \qquad (1)$$

where $$R_0(t) = \begin{cases} R_i & t < T \\ 0 & t \geq T \end{cases} \qquad (2)$$

is the constant activity production rate, T, is the irradiation duration, and $k_i$ is the combined clearance rate of the $i^{th}$ 1 molecular species:

$$k_i = \lambda_{ia} + \lambda_{ib}, \qquad (3)$$

where $\lambda_{ia}$ is the radioactive decay constant, and $\lambda_{ib}$ is the biological washout rate. Of note is that that one radionuclide, when labeled on different molecules would have the radioactive decay constant but a different biological clearance rate. Solving Eqn. 1, the total activity concentration at time t summing all molecules containing proton-induced radionuclides may be written as:

$$A(t) = \sum_i C_i = \begin{cases} \sum_i \frac{R_i}{k_i}(1 - e^{-k_i t}) & t < T \\ \sum_i \frac{R_i}{k_i}(e^{-k_i t} - 1)e^{-k_i t} & t \geq T \end{cases} \qquad (4)$$

In theory, $R_i$ and $k_i$ can be determined by fitting the time course of activity concentration (obtained from dynamic PET reconstructions) from Eqn. 4 using a least-square approach. In practice, to account for imaging duration, the time average of the model prediction may be used in equation (3). In this case, $C_i$ for the $t \geq T$ case can be substituted with $$C_i'(t) = \frac{1}{T_{frame}} \int_{T_0}^{T_0 + T_{frame}} \frac{R_i}{k_i}(e^{-k_i t} - 1)e^{-k_i t} dt \qquad (5)$$

$$= \frac{e^{-k_i T} - 1}{k_i T} \frac{(1 - e^{-k_i T_{frame}})}{k_i T_{frame}}(R_i \cdot T)e^{-k_i T_0}$$

where $T_0$ is the starting point of the time frame and $T_{frame}$ is the time frame length.

In reality, it may not be possible to obtain the exact compositions of the labeled-molecule cocktail in Eqn. 4, and fit for them all, because of image noise and the finite measurement period of the time-activity history. However, it has been shown that 15-O contributes to over 80% of PET signal for the first few minutes after the beam is turned off.

Because of the high water content in human body, it is highly likely that 15-O will form into 15-O-labeled water molecules. With this observation, dynamic data may be fit with one major component representing 15-O—H2O (parameters $R_1$ and $k_1$), and another correction term representing other longer half-life labeled-molecules ($R_2$ and $k_2$). A three-dimensional $R_1$ map can then be obtained by fitting the proton activated volume voxel-by-voxel. As described, such map can be compared with MC predictions for treatment verification.

In addition to descriptions above, specific examples are provided below, in accordance with the present disclosure. These examples are offered for illustrative purposes only, and are not intended to limit the scope of the present invention in any way. Indeed, various modifications in addition to those shown and described herein will become apparent to those skilled in the art from the foregoing description and the following example and fall within the scope of the appended claims.

EXAMPLE

A proof-of-principle study for the evaluation of 15-O production as an imaging target to improve verification of proton treatment plans and study the effects of perfusion.

Methods and Materials: Dynamic PET measurements of irradiation-produced isotopes were taken for a phantom and a rabbit thigh muscle. The rabbit muscle was irradiated and imaged in both live and dead conditions. An operational equation was fitted to the phantom and in vivo data yielding estimates of the 15-O production and clearance rates which was compared live versus dead for the rabbit, and to Monte Carlo (MC) predictions.

Results: PET clearance rates agreed with the decay constants of the dominant radionuclide species in three different materials. In two oxygen-rich materials, the ratio of 15-O production rates agreed with the MC prediction. In the dead rabbit thigh, the dynamic PET concentration histories were accurately described using the 15-O decay constant, while the live thigh activity decayed faster. Most importantly, the 15-O production rates agreed within 2% (p>0.5) in live and dead conditions.

Conclusion: A quantitative measurement of 15-O production and clearance rates in the period immediately following proton therapy was performed. Measurements in the phantom and rabbit were well described in terms of 15-O production and clearance rates, plus a correction for other isotopes. Results shown demonstrate that it is feasible to measure the 15-O production rate for future use in proton therapy verification. In addition, it seems reasonable that 15-O clearance rates may be useful in monitoring permeability changes due to therapy.

Methods

Validation with Phantom Study

Figure 5:
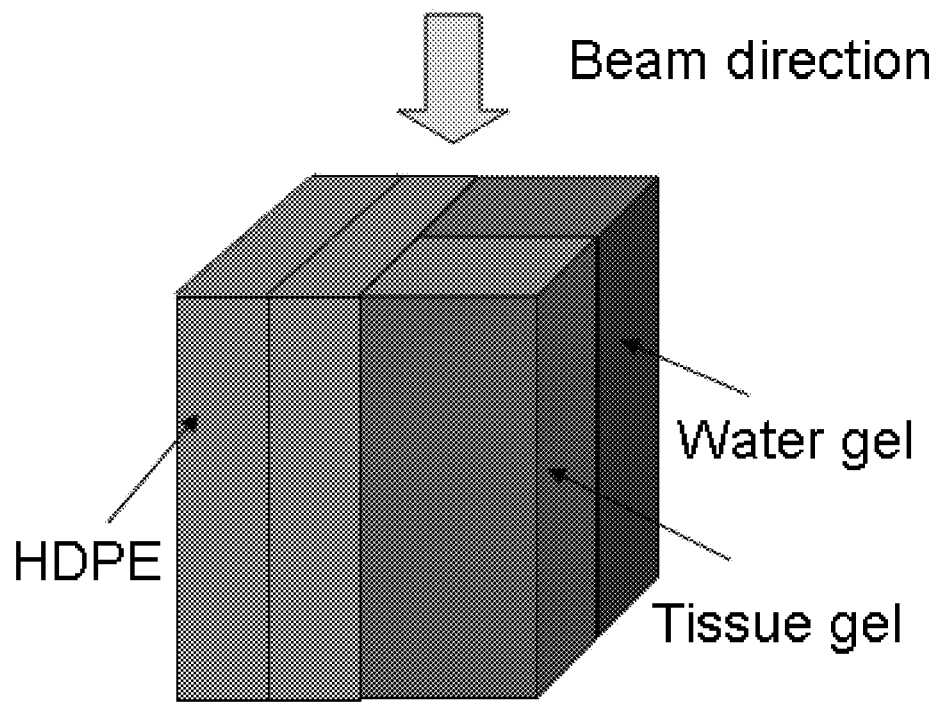
FIG. 5 is an illustration of a phantom used for a study, in accordance with aspects of the present disclosure.

An in-house made phantom was used for the phantom study. The phantom contained three materials: high-density polyethylene (HDPE), gelatinous water (water gel) and tissue equivalent gel (tissue gel). The purpose was to measure the proton activation in carbon-rich, oxygen-rich and tissue-like (realistic carbon/oxygen ratio) materials in parallel. The phantom construction and material properties are shown in FIG. 5.

The phantom was irradiated with a square 7×7 cm2, 2-Gy spread-out Bragg-peak (SOBP) field with a 10-cm water-equivalent (WE) range and a 6-cm WE modulation for 39 seconds. After a 51-second delay, the phantom was imaged in a mobile NeuroPET scanner (PhotoDiagnostic Systems, Inc., PDSi) for 30 minutes in list mode. The list-mode PET data were reconstructed (ordered subset expectation maximization, with 4 subsets and 5 iterations) into 1-minute dynamic frames. The predicted 15-O production rate map was calculated with MC simulations, and smoothed with a 4.6-mm 3-D Gaussian filter to account for the finite spatial resolution of the NeuroPET scanner (4.3 mm) and the positron range of 15-O (~1.5 mm FWHM in water).

In phantom studies, without the presence of biological washout, the expected model-estimated clearance rate is the decay constant (i.e. $k=\lambda_\alpha$) of the dominant radionuclide. Dynamic data were fitted with the kinetic model to test if the model correctly estimates the decay constants of 11-C (HDPE) and 15-O (water and tissue gels). It was also tested if the model correctly estimated the ratio of 15-O production rates for the two oxygen-rich materials, water- and tissue-gel.

Activity concentrations in a large region of interest (ROI) in each material in the flat part of the activity distributions were used to generate time-activity curves (TACs) with low noise. The TACs were fitted with the model to estimate the production and clearance rates of 15-O. The activated volume was also fit voxel-by-voxel to generate the 15-O production rate ($R_1$) map. The estimated $R_1$ maps and 15-O activity production profiles along the beam path were compared with MC predictions from the Geant4-based program TOPAS.

In Vivo Validation

The thigh muscle of a New Zealand White rabbit was irradiated twice, once in the live (perfused) condition and once immediately after sacrificing, in the non-perfused condition, to test two predictions: (1) The 15-O production rates will be the same in the live and dead conditions; and (2) the initial clearance rate, $k_1$, for the dead condition would be equal to the decay constant for 15-O. A 5 Gy SOBP field with range 5 cm and modulation 2 cm was delivered in 268 seconds for each condition, followed by list-mode PET acquisition in a NeuroPET/CT.

The dynamic data in an ROI in the irradiated muscle were fit with the model to determine the 15-O production rate and clearance rate. For the dead, non-perfused, condition (no biological washout), the total clearance rate was compared to the decay constant of 15-O. The model-estimated 15-O production rates for the two conditions were compared with each other by Student's t-test. The irradiated region was also fitted voxel-by-voxel. The expected 15-O production rate distribution was calculated with MC simulations.

Results

Model Validation with the Phantom Study.

Figure 6:
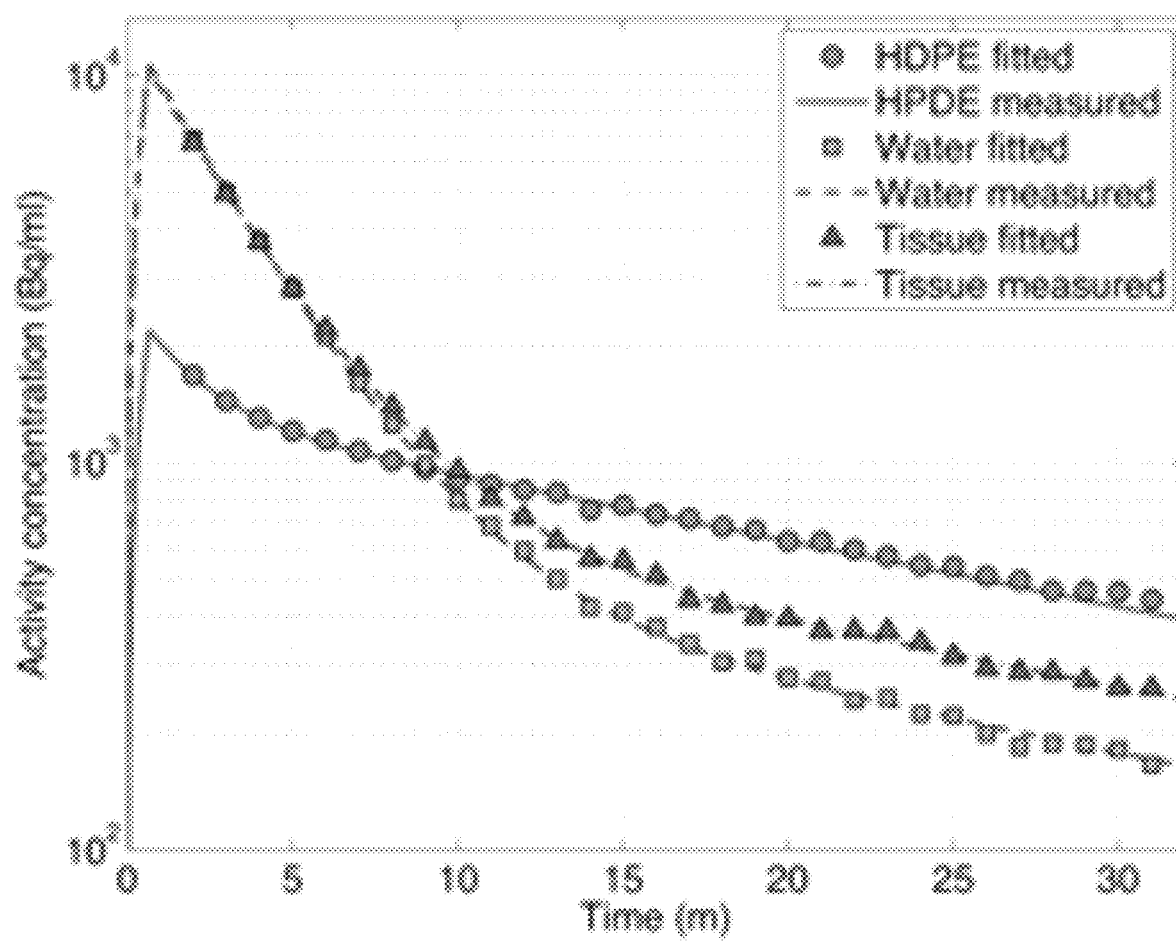
FIG. 6 is a graph showing fitted time-activity curves for materials in the phantom of FIG. 5.

HDPE (high-density polyethylene). The fitted curves for HDPE (C2H4) are shown in FIG. 6. The slight rise of time-activity curve at the beginning is due to the 10C from the 12C(p, p2n)10C reaction channel, which has a half-life of 19 sec. Skipping the first 10 time points and fitting the rest with one k-parameter (when the contribution of 10C can be ignored), the k value (k1=0.0351±0.0004 min$^{-1}$) was very close to the $k_2$ in the 2-parameter case, and in good agreement with the 11-C decay constant.

Tissue-equivalent gel and water gel, containing O, C, N and H. Both water gel and tissue gel have very high oxygen content (87.6% and 73.8%, respectively). The ratio of MC-predicted 15-O production rates in the two materials was 1.05±0.01. All time points of both curves were first fit with two k-parameters to test if the Eqn. 5 model would correctly predict the decay constants. The data and fitting results are shown in FIG. 6.

For both materials, $k_1$ agreed within 3% with the decay constant of 15-O (k1=0.339±0.004 $min^{-1}$ for tissue gel, 0.336±0.003 $min^{-1}$ for water gel, compared to 15-O decay constant of 0.3402 $min^{-1}$). The $k_2$'s were 0.0390±0.0012 $min^{-1}$ for tissue gel and 0.0396±0.0024 $min^{-1}$ for water gel, both between the decay constants of 11-C(0.0340 $min^{-1}$) and 13-N(0.0696 $min^{-1}$). The ratio of production rates ($R_1$'s) for the water and tissue gels was 1.06±0.03, in agreement with the Monte Carlo prediction (p>0.5).

Volume Fitting with the Phantom Study.

The activated volume in the second phantom study was fitted voxel-by-voxel to generate the 15-O production rate ($R_1$) map. The voxel size was 2×2×1.925 $mm^3$ (the original PET image grid). In all the fittings, the $k_2$ parameter was pre-set to 0.039 $min^{-1}$. The fitting results for Eqn. 5 to one slice are compared with MC predictions in FIG. 6-9. The oxygen-rich tissue-gel regions can be clearly distinguished from the low-oxygen HDPE region.

Figure 7:
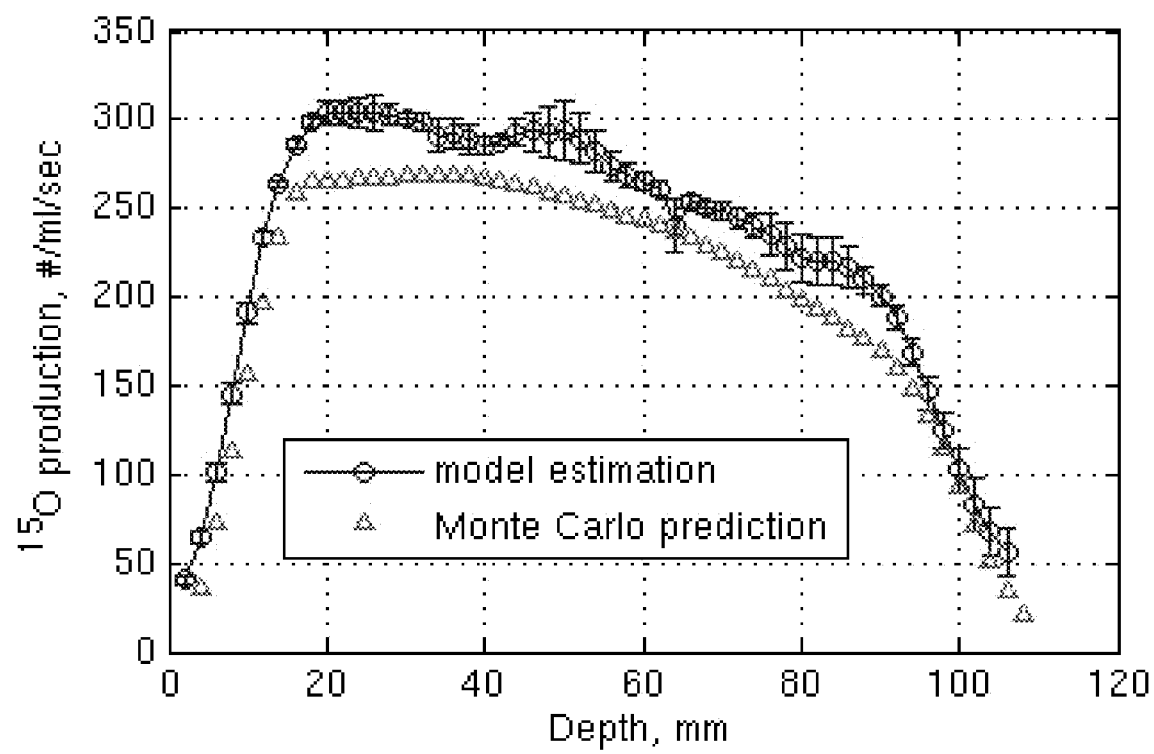
FIG. 7 is a graph comparing an example Monte Carlo predicted 15-O production rate profile compared to a profile generated in accordance with aspects of the present disclosure.
Figure 8:
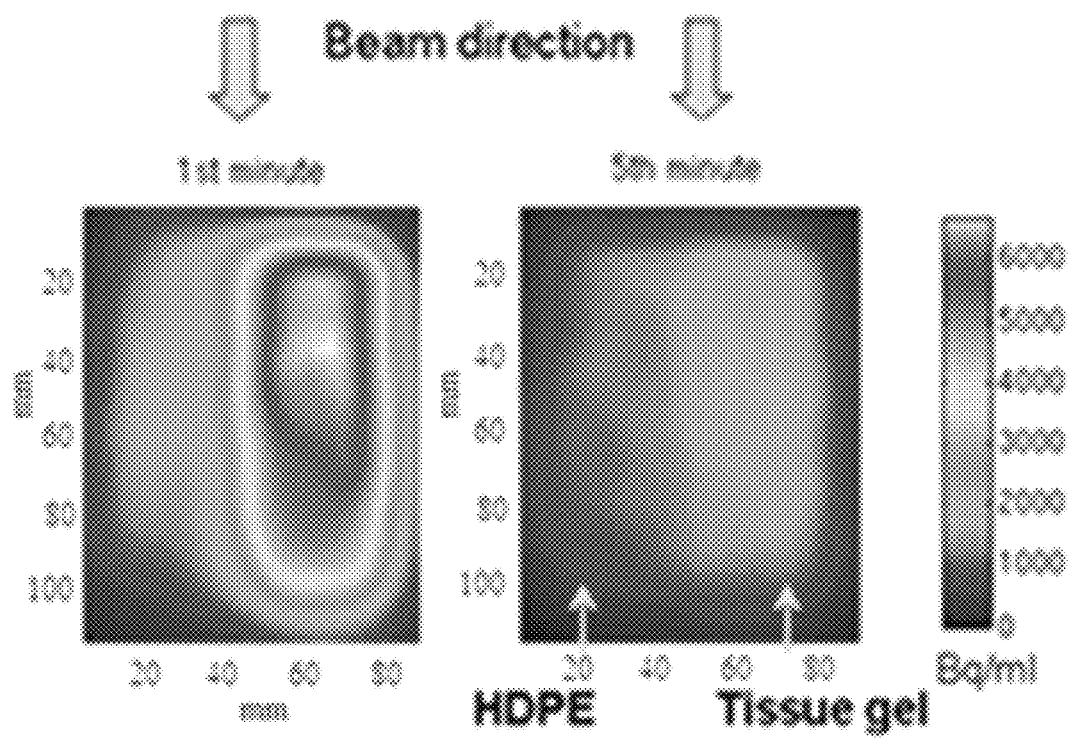
FIG. 8 are positron emission tomography (PET) images obtained using the phantom of FIG. 5 in the first minute and fifth minute of irradiation.
Figure 9:
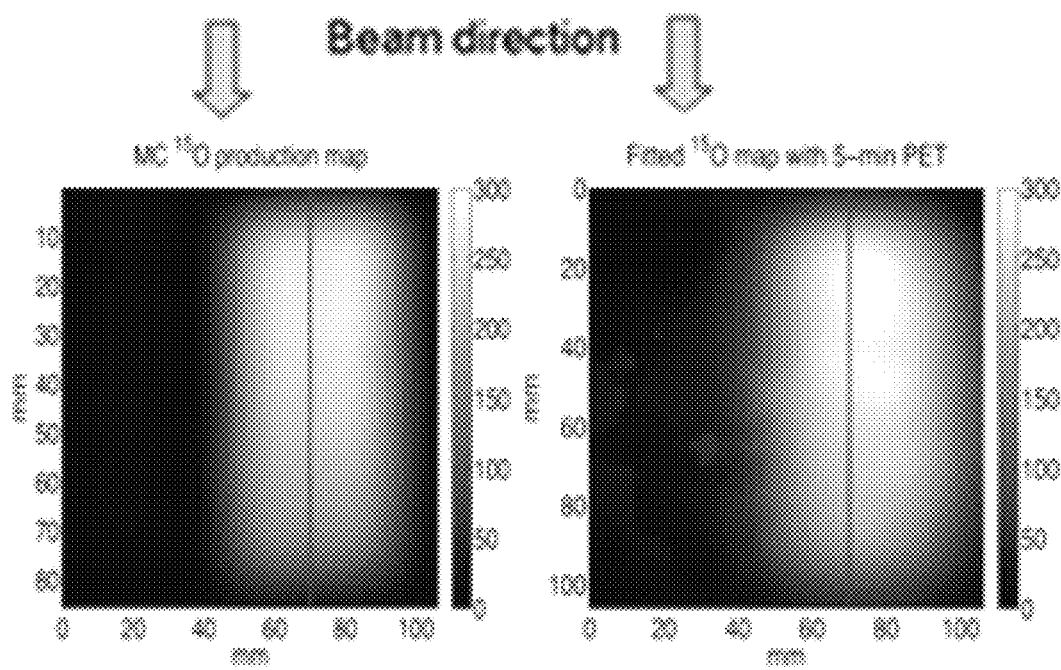
FIG. 9 is a graphical illustration comparing an example Monte Carlo predicted 15-O production rate map compared to a map generated in accordance with aspects of the present disclosure.

The activity production profiles in the tissue gel along the beam path (indicated by the red vertical lines in the images in FIGS. 8 and 9) are shown in FIG. 7. The model estimated and MC predicted activity profiles have the same shape. The 10% discrepancy in absolute quantitation may be attributed to miscalibration of the scanner and uncertainties in cross sections used in the MC simulations.

Model Validation with the Animal Study.

Figure 11:
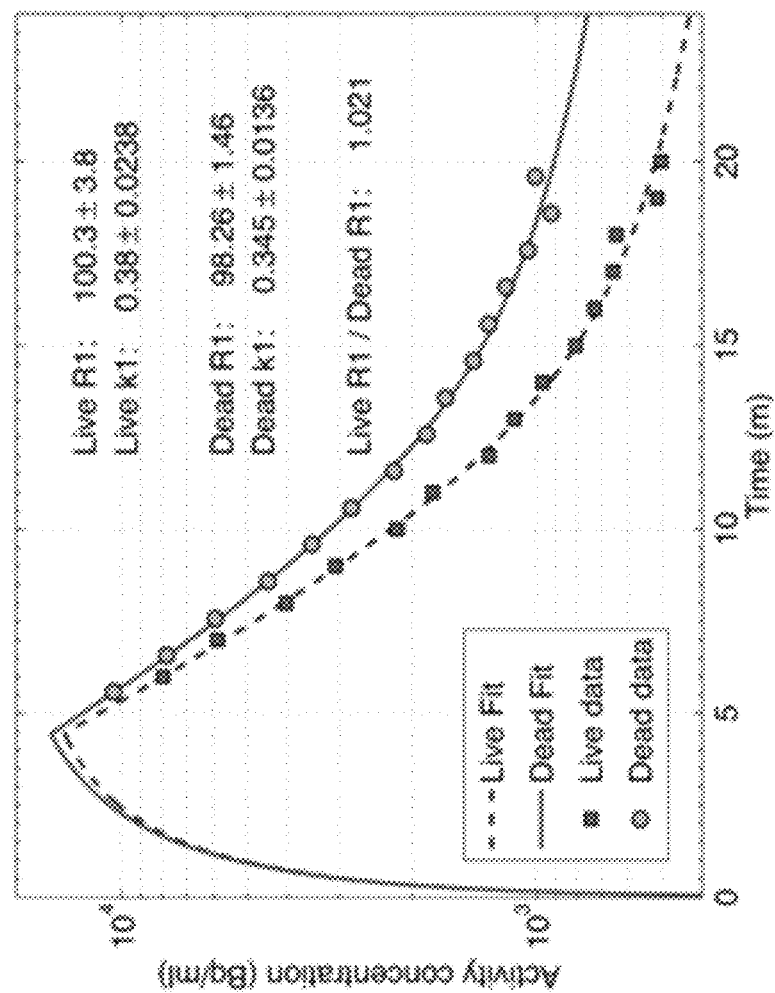
FIG. 11 is a graph showing time activity data acquired from live and dead animals subjected to proton irradiation, in accordance with aspects of the present disclosure.
Figure 10:
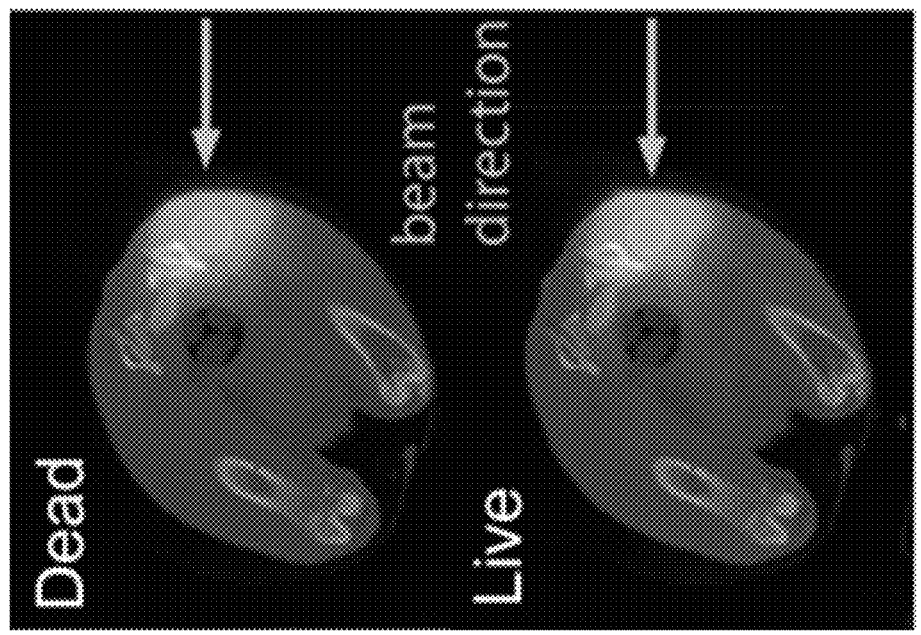
FIG. 10 shows example PET images overlaid on computed tomography (CT) images for a live and dead animals subjected to proton irradiation.
Figure 12A:
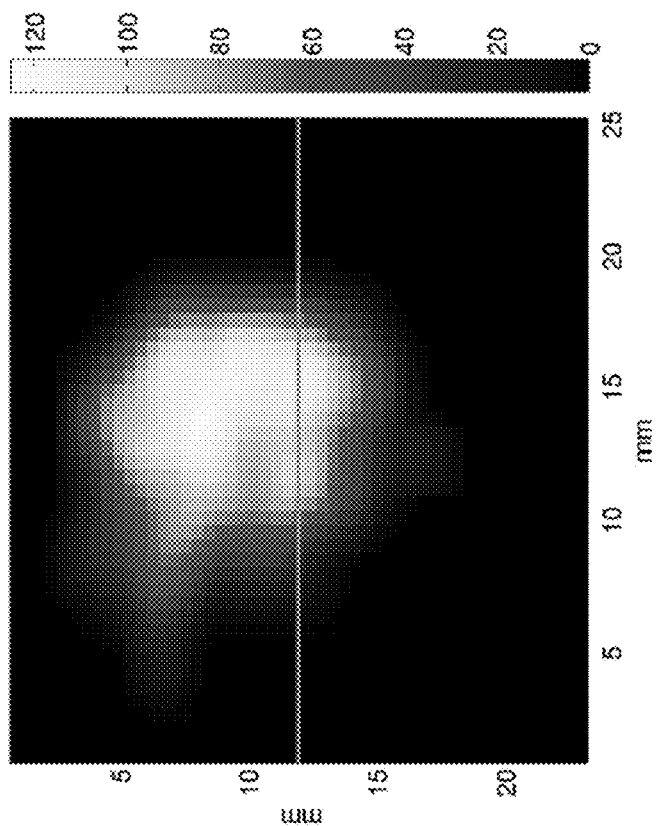
FIG. 12A is an example production rate map for a live animal, obtained in accordance with aspects of the present disclosure.
Figure 12B:
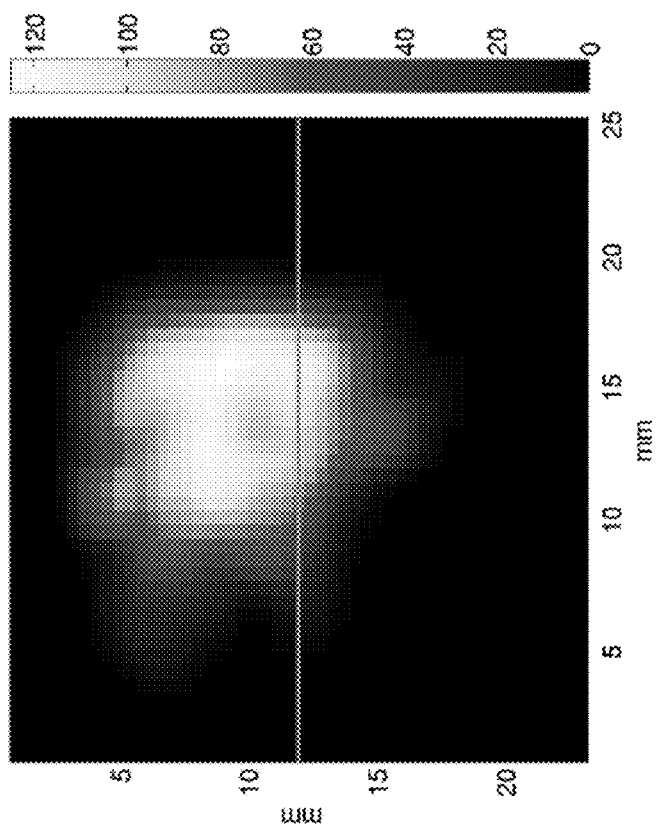
FIG. 12B is an example production rate map for a dead animal, obtained in accordance with aspects of the present disclosure.
Figure 12C:
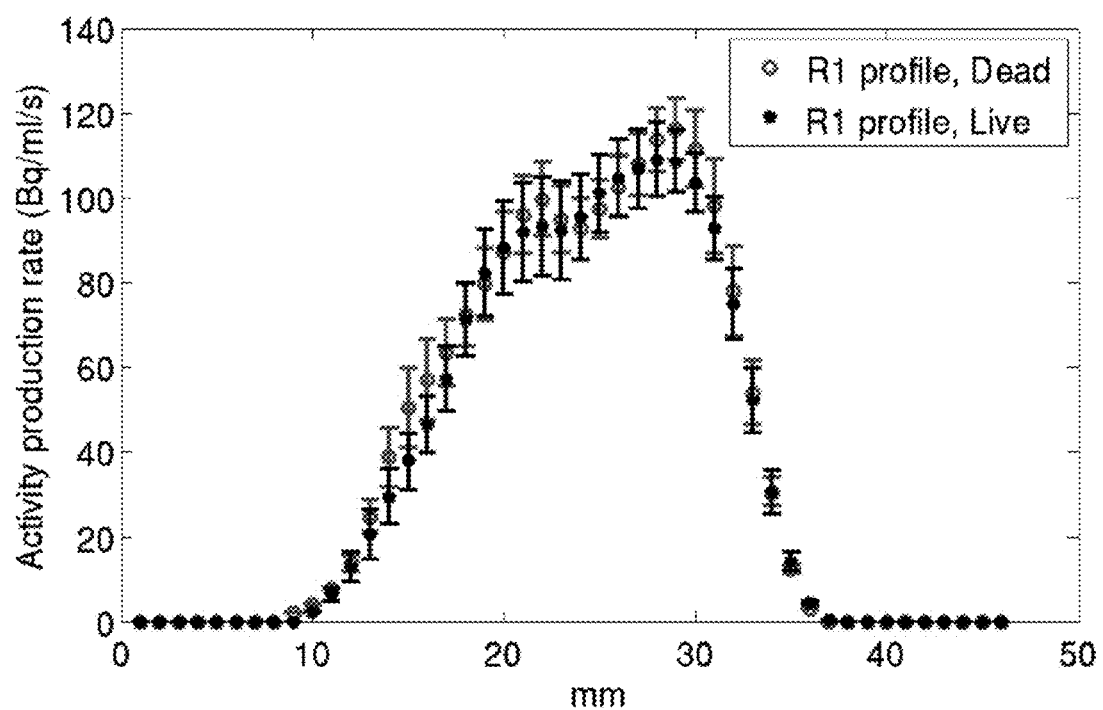
FIG. 12C is a graph comparing production rate profiles for the production rate maps of FIGS. 12A and 12B.

FIG. 10 shows sample PET images of the live (perfused) and dead (non-perfused) rabbit thigh fused with CT. FIG. 11 shows the fitted time-activity curve of the muscle ROI measured in both conditions. The first 15 time points (15-minutes of PET) were fitted with a $k_2$ lower bound of 0.034 $min^{-1}$. The model estimated clearance rate in a region of interest was 0.342±0.014 $min^{-1}$, in excellent agreement with the 15-O decay constant. The live clearance rate was estimated to be 0.396±0.023, greater than the dead clearance rate (one tailed t-test, p=0.1), and giving a biological decay constant of 0.049±0.02 $min^{-1}$. The model-estimated 15-O production rate in the muscle ROI during irradiation was 98±2 Bq/ml/s for the dead condition and 100±4 Bq/ml/s for the live condition, differing by 2±4% (p>0.6). The MC estimated production rate for the same ROI was 87±1 Bq/ml/s. One slice of the fitted 15-O production rate map for the live and dead conditions is shown in FIG. 12A. The activity production profiles along the beam path (indicated by the green horizontal lines) are shown in FIG. 12B. The profiles for the live and dead conditions have a very similar shape, as shown in FIG. 12C. The small differences in amplitude are attributed to repositioning the rabbit and to misregistration of the nonrigid tissue in the rabbit thigh.

Discussion

Because proton-induced PET activity distributions are not directly related to the absorbed dose distribution, PET verification of proton therapy relies on the comparison of MC predictions with PET radioactivity measurements. The general idea has been that the local intensity of a single PET image obtained after treatment shows the extent of the irradiated tissue and that some kind of distal activity threshold can help define proton beam range errors. However, biological washout processes complicate the prediction of dose deposited, beam range, and radioactivity imaged because simple analysis of the image intensities cannot be relied upon to discriminate biological clearance from absence of deposition.

Biological clearance can dramatically change the original proton induced activity distribution, particularly in soft tissue. Previous corrections for biological clearance were applied directly to the Monte Carlo prediction of the measured activity and, as a result, it could not fully account for subject-to-subject variability. Herein, the 15-O-production rate is used as an endpoint. By using dynamic PET measurements, obtained soon after the beam is turned off, both the 15-O production rate and the clearance rate of water can be estimated. The advantage of this approach is that a MC prediction (in absolute units) can be directly compared with the PET measurement in absolute units. It is envisioned that future development of this comparison will allow the MC prediction of 15-O production thresholds to quantify beam range measurements.

In theory, by fitting the proton activated volume voxel-by-voxel, a three-dimensional R map can be obtained, which can be compared with a MC-predicted 15-O production distribution for treatment verification. The results shown suggest it is feasible to obtain the original 15-O distribution from dynamic reconstruction data. Good agreement with MC predictions in relative activity distributions can be obtained with 10-15 minutes of PET acquisition soon after proton irradiation in phantom and animal studies. A remaining discrepancy between the MC and PET predicted production rates in the rabbit study may be attributed to uncertainties in the cross-sections and CT numbers used in the MC calculation. More importantly, as expected, the same $R_1$ value was recovered for both live and dead conditions in the rabbit for the same irradiation, indicating that the model can correct for biological clearance effects. FIG. 7 illustrates the power of this approach.

By comparing the profile of measured and predicted production rates, the local dose deposited and the beam profile can be measured quantitatively. In addition to the 15-O production rate map, the present approach produces a map of the water clearance rate, which can potentially be used for the evaluation of tumor response to therapy during fractionated treatments. The washout pattern of proton produced activity is related to perfusion and the biological environment of tumors and tissues. Factors affecting clearance rate include the local vasculature development and possibly local changes in the permeability of water. After several treatments, tumor perfusion and/or permeability may change as a response to the therapy. These changes in washout patterns may carry useful biological information that can be used to individualize therapy to optimize treatment response.

The new approach described herein relies on well-established principles—the conservation of tracer mass and the compartment modeling of the clearance of labeled water. A general theory was presented that may be applicable to any time epoch following, or even during, treatment. Further analysis suggests that there is significant advantage to imaging when the dynamic PET data can be represented as the clearance of water, with nominal correction for 11-C-labeled molecules.

One might be tempted to base a similar analysis on the clearance of 11-C, but due to the biochemistry, it is likely that 11-C is incorporated into many molecules with widely varying clearance rates. The observed mixtures of 11-C compounds will likely vary greatly, depending on exactly when the measurements commence. Rapidly clearing 11-C-compounds may not be measured, leading to errors in the 11-C production rate.

In summary, a novel system and method for the measurement of 15-O production and clearance, and possible other positron emitting radionuclides, suitable for verifying the treatment delivery in patients undergoing proton beam therapy.

The present invention has been described in terms of one or more preferred embodiments, and it should be appreciated that many equivalents, alternatives, variations, and modifications, aside from those expressly stated, are possible and within the scope of the invention.

We claim:

1. A method for quantifying radioactivity production during a proton treatment of a patient, the method comprising:
   (a) administering, using a proton delivery system, a proton treatment using at least one therapeutic proton beam generating positron emitting radionuclides within a region of interest (ROI) of a patient;
   (b) acquiring, using an emission tomography system, emission tomography data indicative of an activity of the positron emitting radionuclides in the ROI;
   (c) quantifying, based on a time averaged kinetic model relating to radioactivity production rate caused by proton beams in a biological subject and a time averaged clearance rate in the biological subject, a radioactivity production rate of at least one of the positron emitting radionuclides using the emission tomography data; and
   (d) generating at least one map indicative of the radioactivity production rate of the at least one positron emitting radionuclide.

2. The method of claim 1, wherein the positron emitting radionuclides include at least one of 15-O, 13-N, or 11-C, or a combination thereof.

3. The method of claim 1, wherein the emission tomography system comprises a positron emission tomography (PET) system, a single photon emission computed tomography (SPECT) system, a hybrid computed tomography (CT)/PET system, or a hybrid magnetic resonance (MR)/PET system.

4. The method of claim 1, wherein the emission tomography data is acquired after a preselected time interval following the proton treatment.

5. The method of claim 4, wherein the preselected time interval is up to 20 minutes.

6. The method of claim 4, wherein the preselected time interval is selected to maximize emission tomography signals from 15-O.

7. The method of claim 1, wherein the method further comprises generating a time series of emission tomography images using the emission tomography data.

8. The method of claim 1, wherein the time averaged kinetic model comprises the time averaged clearance rate of the at least one positron emitting radionuclide.

9. The method of claim 8, wherein the time averaged clearance rate includes a radioactive decay and a biological washout.

10. The method of claim 1, wherein the method further comprises analyzing the at least one map to determine information associated with the administered at least one therapeutic proton beam.

11. The method of claim 10, wherein the information comprises a penetration depth of the at least one therapeutic proton beam.

12. The method of claim 10, wherein the information is utilized to adapt a treatment plan.

13. The method of claim 1, wherein the emission tomography data is acquired during the proton treatment.

14. The method of claim 1, wherein the time averaged kinetic model is of the form:

$$\frac{dC_i}{dt} = R_0(t) - k_i C_i$$

$$R_0(t) = \begin{cases} R_i & t < T \\ 0 & t \geq T \end{cases}$$

where $C_i$ represents a concentration of an $i^{th}$ labeled molecule, t is time, $R_0(t)$ represents a constant activity production rate, $R_i$ represents an activity concentration for the $i^{th}$ labeled molecule, T represents an irradiation duration, and $k_i$ represents a combined clearance rate of radioactive decay and biological washout for an $i^{th}$ molecular species.

15. the method of claim 14, wherein the time averaged kinetic model is a total activity concentration at time t of the form:

$$A(t) = \sum_i C_i = \begin{cases} \sum_i \frac{R_i}{k_i}(1 - e^{-k_i t}) & t < T \\ \frac{e^{-k_i t} - 1}{k_i t} \frac{\left(1 - e^{-k_i T_{frame}}\right)}{k_i T_{frame}} (R_i \cdot T) e^{-k_i T_0} & t \geq T \end{cases}$$

where $T_0$ represents a starting point of a time frame, and $T_{frame}$ represents a time frame length.

16. The method of claim 1, further comprising generating a water clearance map for an evaluation of tumor response.

17. A system for quantifying radioactivity production during a proton treatment of a patient, the system comprising:
   a proton delivery system configured to deliver a proton treatment using at least one therapeutic proton beam generating positron emitting radionuclides within a region of interest (ROI) of a patient;
   an emission tomography system configured to acquire emission tomography data indicative of an activity of the positron emitting radionuclides;
   at least one processor configured to:
      receive the emission tomography data;
      quantify, based on a time averaged kinetic model relating to radioactivity production rate caused by proton beams in a biological subject and time averaged clearance rate in the biological subject, a radioactivity production rate of at least one of the positron emitting radionuclides using the emission tomography data; and
      generate at least one map indicative of the radioactivity production rate of the at least one of positron emitting radionuclides.

18. The system of claim 17, wherein the positron emitting radionuclides include at least one of 15-O, 13-N, or 11-C, or a combination thereof.

19. The system of claim 17, wherein the emission tomography system comprises a positron emission tomography (PET) system, a single photon emission computed tomography (SPECT) system, a hybrid computed tomography (CT)/PET system, or a hybrid magnetic resonance (MR)/PET system.

20. The system of claim 17, wherein the emission tomography data is acquired during the proton treatment or after a preselected time interval following the proton treatment.

21. The system of claim 17, wherein the at least one processor is further configured to generate a time series of emission tomography images using the emission tomography data.

22. The system of claim 17, wherein the time averaged kinetic model comprises the time averaged clearance rate of the at least one positron emitting radionuclide.

23. The system of claim 22, wherein the time averaged clearance rate includes a radioactive decay and a biological washout.

24. The system of claim 17, wherein the at least one processor is further configured to analyze the at least one map to determine information associated with at least one therapeutic proton beam delivered by proton delivery system within the ROI of the patient.

25. The system of claim 24, wherein the information comprises a penetration depth of the at least one therapeutic proton beam.

26. The system of claim 25, wherein the information is utilized to adapt a treatment plan.

27. The system of claim 25, wherein the information is utilized to determine a response of the patient to the proton treatment.

28. The system of claim 17, wherein the time averaged kinetic model is of the form:

$$\frac{dC_i}{dt} = R_0(t) - k_i C_i$$

$$R_0(t) = \begin{cases} R_i & t < T \\ 0 & t \geq T \end{cases}$$

where $C_i$ represents a concentration of an $i^{th}$ labeled molecule, t is time, $R_0(t)$ represents a constant activity production rate, $R_i$ represents an activity concentration for the $i^{th}$ labeled molecule, T represents an irradiation duration, and $k_i$ represents a combined clearance rate of radioactive decay and biological washout for an $i^{th}$ molecular species.

29. the system of claim 28, wherein the time averaged kinetic model is a total activity concentration at time t of the form:

$$A(t) = \sum_i C_i = \begin{cases} \sum_i \frac{R_i}{k_i}(1 - e^{-k_i t}) & t < T \\ \frac{e^{-k_i t} - 1}{k_i t} \frac{(1 - e^{-k_i T_{frame}})}{k_i T_{frame}} (R_i \cdot T) e^{-k_i T_0} & t \geq T \end{cases}$$

where $T_0$ represents a starting point of a time frame, and $T_{frame}$ represents a time frame length.

30. The system of claim 17, wherein the at least one processor is further configured to generate a water clearance map for an evaluation of tumor response.

31. A non-transitory, computer-readable storage medium having stored thereon instructions that, when executed by a computer processor, cause the computer processor to generate a report indicative of radioactivity production during a proton treatment of a patient, the instructions comprising:

(a) accessing emission tomography data indicative of an activity of at least one positron emitting radionuclide generated in a region of interest (ROI) of a patient using at least one therapeutic proton beam;

(b) quantifying, based on a time averaged kinetic model relating to radioactivity production rate caused by proton beams in a biological subject and a time averaged clearance rate in the biological subject, a radioactivity production rate of at least the at least one positron emitting radionuclide using the emission tomography data; and (c) generating a report indicative of the radioactivity production rate of the at least one positron emitting radionuclide.

32. The computer-readable storage medium of claim 31, wherein the positron emitting radionuclides include at least one of 15-O, 13-N, or 11-C, or a combination thereof.

33. The computer-readable storage medium of claim 31, wherein the time averaged kinetic model comprises the time averaged clearance rate of the at least one positron emitting radionuclide.

34. The computer-readable storage medium of claim 33, wherein the time averaged clearance rate includes a radioactive decay and a biological washout.

35. The computer-readable storage medium of claim 31 further comprising analyzing at least one map generated using the radioactivity production rate of the at least one positron emitting radionuclide to determine information associated with the at least one therapeutic proton beam.

36. The computer-readable storage medium of claim 31, wherein the time averaged kinetic model is of the form:

$$\frac{dC_i}{dt} = R_0(t) - k_i C_i$$

$$R_0(t) = \begin{cases} R_i & t < T \\ 0 & t \geq T \end{cases}$$

where $C_i$ represents a concentration of an $i^{th}$ labeled molecule, t is time, $R_0(t)$ represents a constant activity production rate, $R_i$ represents an activity concentration for the $i^{th}$ labeled molecule, T represents an irradiation duration, and $k_i$ represents a combined clearance rate of radioactive decay and biological washout for an $i^{th}$ molecular species.

37. The computer-readable storage medium of claim 36, wherein the time averaged kinetic model is a total activity concentration at time t of the form:

$$A(t) = \sum_i C_i = \begin{cases} \sum_i \frac{R_i}{k_i}(1 - e^{-k_i t}) & t < T \\ \frac{e^{-k_i t} - 1}{k_i t} \frac{(1 - e^{-k_i T_{frame}})}{k_i T_{frame}} (R_i \cdot T) e^{-k_i T_0} & t \geq T \end{cases}$$

where $T_0$ represents a starting point of a time frame, and $T_{frame}$ represents a time frame length.

38. The computer-readable storage medium of claim 31, further comprising generating a water clearance map for an evaluation of tumor response.

* * * * *